United States Patent [19]

Neitz et al.

[11] Patent Number: 5,837,461

[45] Date of Patent: Nov. 17, 1998

[54] DETECTION OF CONE-PHOTORECEPTOR-BASED VISION DISORDERS

[75] Inventors: Maureen E. Neitz; John F. Neitz, both of New Berlin, Wis.

[73] Assignee: MCW Research Foundation, Milwaukee, Wis.

[21] Appl. No.: 739,401

[22] Filed: Oct. 31, 1996

[51] Int. Cl.$^6$ .......................................... C12Q 1/68
[52] U.S. Cl. ................. 435/6; 436/15; 530/324; 530/350
[58] Field of Search ................. 435/6; 530/350, 530/324; 436/15

[56] References Cited

PUBLICATIONS

D.T. Lindsey, et al., "Individual Differences in Rayleigh Matches are Related to Differences in L Cone Pigment Structure," University of Washington, pp. 17–19.
Neitz et al, Invest. Opthal. Vis. Sci. 37(3): 5448 (1996), Abstract.
Kainz et al, Invest. Opthal. Vis. Sci. 37(3): 5448 (1996), Abstract.
Neitz et al, in Molecular Genetics of Inherited Eye Disorders, 1994, Wright et al (Eds.), Modern Genetics Book Series, Harwood Academic Publishers, Chur, Switzerland, pp. 217–257.
Neitz et al, The molecular genetic basis of polymorphism in normal color vision, Advances in Color Vision, Journal of the Optical Society of America, Technical Digest Series, 4: 14–16 (1992).
The Lancet, London and Baltimore Saturday 3 Feb. 1990, vol. 335, No. 8684.
A.B. Asenjo, et al., "Molecular Determinants of Human Red/Green Color Discrimination," Neuron 12:1131–1138, 1994.
S.D. Balding, et al., "Cone Opsin Gene Expression in Mend with Color Vision in Infants and Adults," Invest. Ophtham. Vis. Sci. 38(4):S14, 1997 (Abstract).
M.L. Biber, et al., "Comparison of Genetic and Phenotypic Markers of Color Vision in Infants and Adults," Invest. Ophtham. Vis. Sci. 38(4):S14, 1997 (Abstract).
A.C. Bird, "Retinal Photoreceptor Dystrophies LI. Edward Jackson Memorial Lecture," Am. J. Ophthalm. 119(5):543–562, 1995.
C.A. Curcio, et al., "Photoreceptor Loss in Age–Related Macular Degeneration," Invest. Ophthalm. Vis. Sci. 37(7):1236–1249, 1996.
S.S. Deeb, et al., "Genotype–Phenotype Relationships in Human Red/Green Color–Vision Defects: Molecular and Psychophysical Studies," Am. J. Hum. Genet. 51:687–700, 1992.
S.S. Deeb, et al., "Structure–function relationships in human red/green color vision," Col. Vis. Def. XI:13–17, 1993.
S.A. Hagstrom, et al., "Four Different Cone Types in a Human Eye Identified from mRNA in Individual Photoreceptors," Invest. Ophtham. Vis. Sci 36(4):S1054, 1995 (Abstract).
G.H. Jacobs and Jay Neitz, "ERG flicker photometric evaluation of spectral sensitivity in protanopes and protanomalous trichromats," Col. Vis. Def. XI:25–31, 1993.
G.H. Jacobs, et al., "Mutations in S–cone pigment genes and the absence of colour vision in two species of nocturnal primate," Proc. R. Soc. Lond. B 263:705–710, 1996.
P.M. Kainz, et al., "Region between the X–Linked Photopigment Genes Shares Homology with Regions within the Genes," Invest. Ophtham. Vis. Sci. 35(4):1262, 1994 (Abstract).
P.M. Kainz, et al., "Numbers and Ratios of X–Lined Pigment Genes Underlying Deuteranomaly," Invest. Ophtham. Vis. Sci. 36(4):S889, 1995 (Abstract).
P.M. Kainz, et al., "Molecular Detection of Female Carrier of Protan Color Vision Defects," Invest. Ophtham. Vis. Sci. 38(4):S1015, 1997 (Abstract).
U. Kellner, et al., "Selective Cone Dystrophy With Protan Genotype," Invest. Ophtham. Vis. Sci. 36(12):2381–2387, 1995.
S.L. Merbs and J. Nathans, "Absorption spectra of human cone pigments," Nature 356:433–435, 1992.
S.L. Merbs and J. Nathans, "Absorption Spectra of the Hybrid Pigments Responsible for Anomalous Color Vision," Science 258:464–466, 1992.
J. Mollon, "Worlds of Difference," Nature vol. 356, 1992.
J. Mollon, "Mixing genes and mixing colours," Curr. Biol. 3(2):82–85, 1993.
J. Nathans, et al., "Molecular Genetics of Human Color Vision: The Genes Encoding Blue, Green, and Red Pigments," Science 232:193–202, 1986.
J. Nathans, et al., "Molecular Genetics of Inherited Variation in Human Color Vision," Science 232:203–210, 1986.
J. Nathans, et al., "Molecular Genetics of Human Blue Cone Monochromacy," Science 245:831–838, 1989.
J. Nathans, et al., "Molecular Genetics of Human Visual Pigments," Annu. Rev. Genet. 26:403–424, 1992.
J. Nathans, et al., "Genetic Heterogeneity among Blue–Cone Monochromats," Am. J. Hum. Genet. 53:987–1000, 1993.
J. Nathans, "In the Eye of the Beholder: Visual Pigments and Inherited Variation in Human Vision," Cell 78:357–360, 1994.
J. Neitz and G.H. Jacobs, "Further Observations on Variations in Color Matching Among Normal Males," Vis. Psycho., p. 299, Poster Presentation (Abstract).
M. Neitz and J. Neitz, "Males Usually have more than One L Pigment Gene," Vis. Psycho., p. 754, Paper Presentation (Abstract).
J. Neitz and M. Neitz, "Do People with Anomalous Color Vision have Anomalous Pigments?" Vis. Psycho., p. 754, Paper Presentation (Abstract).

(List continued on next page.)

Primary Examiner—James Martinell
Attorney, Agent, or Firm—Quarles & Brady

[57] ABSTRACT

A method of detecting cone-photoreceptor-based vision disorders is disclosed. In one embodiment, the method comprises the steps of examining the amino acid sequences of a patient's L or M photopigments and correlating the amino acid combinations associated with vision disorder.

6 Claims, 6 Drawing Sheets

OTHER PUBLICATIONS

J. Neitz, et al., "Matches from Normal Trichromatic Males Suggest some Eyes Contain more than Three Cone Types," *Vis. Psycho.*, p. 1092, Paper Presentation (Abstract).

J. Neitz and M. Neitz, "All Common Red–Green Color Defects can be explained as arising by the same Simple Mechanism," *Cones Genet. Col. Vis.* p. 911 (Abstract).

M. Neitz and J. Neitz, "Individual Males can Express Five Different Cone Pigment Genes," *Cones Genet. Col. Vis.* p. 911 (Abstract).

J. Neitz and G.H. Jacobs, "Polymorphism of Cone Pigments among Color Normals: Evidence from Color Matching," B. Drum and G. Varriest (eds.), Colour Vision Deficiencies, Kluwer Academic Publishers, pp. 27–34, 1989.

J. Netiz, et al., "Analysis of fusion gene and encoded photopigment of colour–blind humans," *Nature* 342 (6250:679–682, 1989).

J. Neitz and G.H. Jacobs, "Polymorphism in Normal Human Color Vision and its Mechanism," *Vision Res.* 30(4):621–636, 1990.

M. Neitz, et al., "Spectral Tuning of Pigments Underlying Red–Green Color Vision," *Science* 252:971–974, 1991.

M. Neitz, et al., "Relationship between cone pigments and genes in deuteranomalous subjects," B. Drum, J.D. Moreland & A. Serra (eds.), Colour Vision Deficiencies, pp. 397–403, 1991.

J. Neitz, et al., "More than Three Different Cone Pigments Among People with Normal Color Vision," *Vision Res.* 33(1):117–122, 1993.

M. Neitz, and J. Neitz, "Long–Wave Pigment Gene Number varies across Color Normal Males," *Invest. Ophtham. Vis. Sci.* 35(4):1710, 1994 (Abstract).

M. Neitz and J. Neitz, "Numbers and Ratios of Visual Pigment Genes for Normal Red–Green Color Vision," *Science* 267:1013–1016, 1995.

M. Neitz, et al., "Genetic Basis of Photopigment Variations in Human Dichromats," *Vision Res.* 35915):2095–2013, 1995.

M. Neitz, et al., "Polymorphism in the Number of Genes Encoding Long–wavelength–sensitive Cone Pigments Among Males with Normal Color Vision," *Vision Res.* 35(17):2395–2407, 1995.

M. Neitz and J. Neitz, "Deduced Amino Acid Sequences of Cone Pigments from Two Species of Squirrel: A Spectral Tuning Study," *Invest. Ophtham. Vis. Sci.* 36(4):S889, 1995 (Abstract).

J. Neitz, et al., "Visual Pigment Gene Structure and the Severity of Color Vision Defects," *Science* 274:801–804, 1996.

M. Neitz and J. Neitz, "Variety of photopigment genes underlying red–green colour vision," C.R. Cavanius (ed.), Colour Deficiencies, pp. 33–43, 1997.

E. Reichel, et al., "An Electroretinographic and Molecular Genetic Study of X–Linked Cone Degeneration," *Am. J. Ophthalm.* 108:540–547, 1989.

S.A. Sjoberg, et al., "Structures of the L and M Visual Pigment Genes Expression in Normal Color Vision," *Invest. Ophtham. Vis. Sci.* 38(4):S14, 1997 (Abstract).

S. Strege, et al., "Cone Opsin Gene Expression in the Retinas of Men with Two Different L Cone Pigment Genes," *Invest. Ophtham. Vis. Sci.* 37(3):S448, 1996 (Abstract).

J. Winderickx, et al., "Polymorphism in red photopigment underlies variation in colour matching," *Nature* 356:431–433, 1992.

J. Winderickx, et al., "Defective colour vision associated with a missense mutation in the human green visual pigment gene," *Nature Genet.* 1:251–256, 1992.

T. Yamaguchi, et al., "Levels of expression of the red, green and green–red hybrid pigment genes in the human retina," C.R. Cavonius (ed.), Colour Vision Deficiencies, pp. 21–31, 1997.

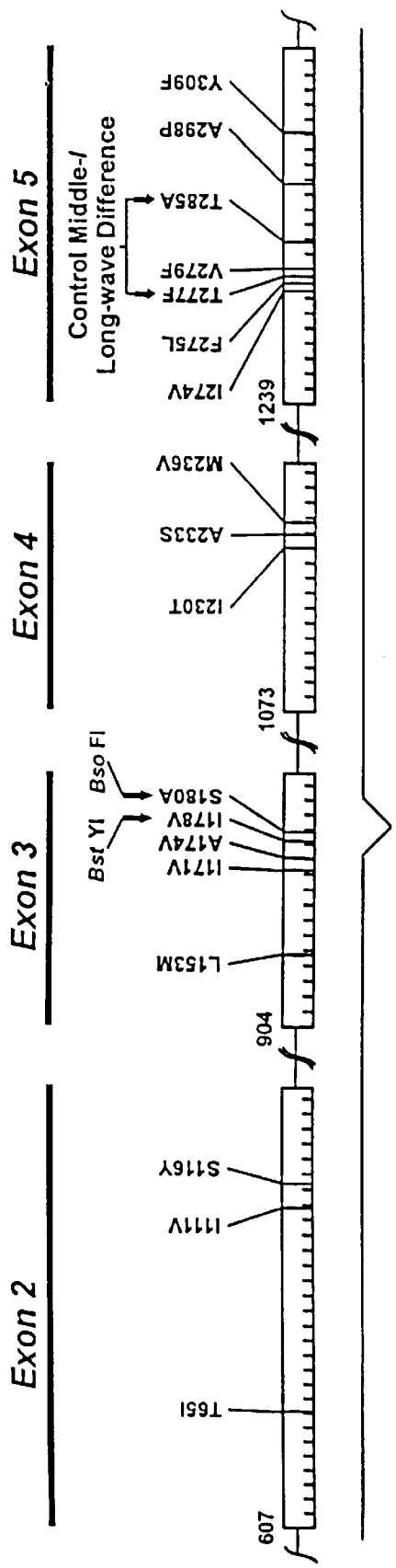
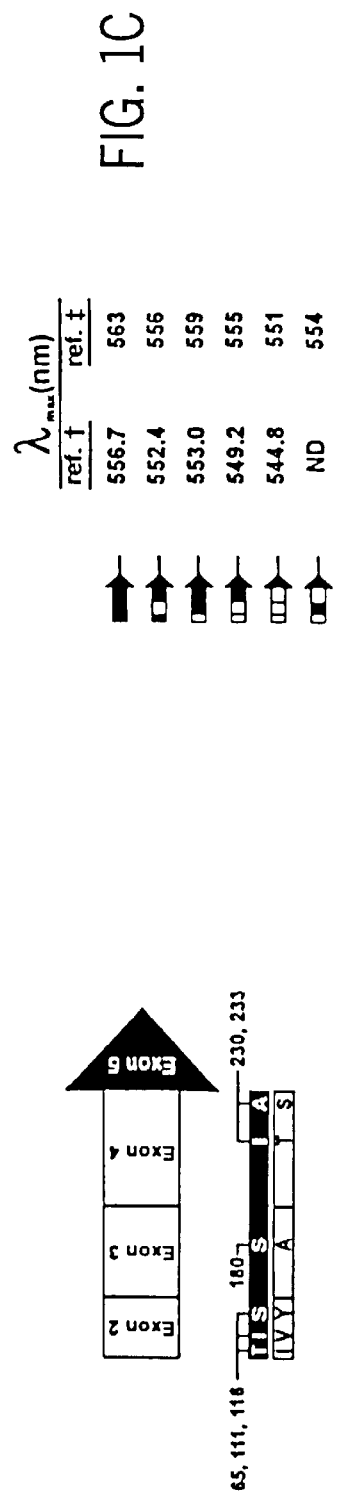
FIG. 1A
FIG. 1B
FIG. 1C

FIG. 2

| | SUBJECTS | GENE ARRANGEMENTS FROM SOUTHERNS | CODON 180 A=ala S=ser 1ST GENE | DOWNSTREAM HYBRID GENES | DIFFERENCES? Y=yes N=no EXONS 4 3 2 | GENE ARRANGEMENT (THIS STUDY) | PREDICTED SPECTRAL SEPARATION | D OF MOST DIFFICULT PLATE READ |
|---|---|---|---|---|---|---|---|---|
| DICHRO-MATS | d2 | | A | — | — — N | | 0.0 | >0.081 |
| | d1 | | S | — | — — N | | 0.0 | >0.081 |
| VERY SEVERE | 189 | | A | S | N Y Y | (65, 111, 116) | $-0.6^{\dagger}, -3^{\ddagger}$ | >0.081 |
| SEVERE | 187 | | S | S | N N N | | $3.7^{\dagger}, -4^{\ddagger}$ | 0.081 |
| | 021 | | A | A | N N N | | $1^{\ddagger}, -3.6^{\dagger}$ | 0.081 |
| | 012 | | A | A | N N N | | $1^{\ddagger}, -3.6^{\dagger}$ | 0.072 |
| | 022 | | S | S | N N N | | $1^{\ddagger}, -3.6^{\dagger}$ | 0.072 |
| | 188 | | A | A | N N N | | $3.7^{\dagger}, -4^{\ddagger}$ | 0.072 |
| | 176 | | | | N N Y | | $1^{\ddagger}, -3.6^{\dagger}$ | 0.072 |
| MILD | 191 | | A | A | Y N Y* | | $5^{\ddagger}, -7.6^{\dagger}$ | 0.032 |
| | 185 | | A | A | Y N Y* | | $5^{\ddagger}, -7.6^{\dagger}$ | 0.032 |
| | 027 | | A | A,S | Y N Y | | $5^{\ddagger}, -7.6^{\dagger}$ | 0.032 |
| | 028 | | S | A,S | N Y Y* | | $7.9^{\dagger}, -8^{\ddagger}$ | 0.032 |
| VERY MILD | 009 | | S | A | Y Y Y* | | $11.9^{\dagger}, -12^{\ddagger}$ | 0.022 |
| | 186 | | S | A | Y Y Y* | | $11.9^{\dagger}, -12^{\ddagger}$ | 0.022 |
| | 017 | | S | A,S | Y Y Y* | | $11.9^{\dagger}, -12^{\ddagger}$ | 0.022 |
| | 190 | | S | A,S | Y Y Y* | | $11.9^{\dagger}, -12^{\ddagger}$ | 0.022 |
| | 182 | | S | S | Y N Y* | | $9^{\ddagger}$ | 0.022 |

FIG. 6

DETECTION OF CONE-PHOTORECEPTOR-BASED VISION DISORDERS

FIELD OF THE INVENTION

The field of the present invention is detection of vision-based disorders by examination of the M and L visual pigment genes.

BACKGROUND OF THE INVENTION

Normal daylight vision is mediated by three classes of light sensitive cells (called "cone photoreceptors" or "cones") in the eye. More than just providing daylight vision, the cone photoreceptors also provide color vision. Each class of cone is sensitive to a different region of the visible spectrum and thus the different classes are technically referred to as the short-, middle-, and long-wavelength sensitive cones, or the S-, M- and L-cones, respectively. They are more commonly referred to as the blue, green and red cones, abbreviated here B-, G- and R-cones. The photopigment is the molecule within the cone photoreceptor that is responsible for absorbing light, and conferring the spectral characteristics on a particular cone cell. The photopigments are transmembrane proteins, and within each cone cell, the major protein present is the photopigment. Because it is imbedded in the cell membrane and represents the majority of the protein within cone cells, the photopigment molecule is a critical structural component of the cone cells. Disruption of the normal structure or function of the photopigment will disrupt the structure or function of the cone photoreceptor. Retinal degeneration can follow from abnormalities in the structure of a large number of cone cells. In the eye, about 7–8% of the cones are B-cones. The remaining 92–93% of the cones are red and green cones. The blue, red and green cone pigments are all quite similar to one However, the blue cone is only about 43% identical in amino acid sequence to the red and green cone pigments while the red and green pigments are more nearly identical to each other in amino acid sequence.

The genes for the red and green cone pigments are arranged in a head-to-tail tandem array on the X-chromosome. Across individuals there is variation in the number of red and in the number of green pigment genes. Each gene is comprised of 6 exons. Exon 1 and exon 6 of the red and green pigment genes are identical. Exons 2, 3, 4 and 5 of the genes each specify amino acid dimorphisms. The amino acid sequences of the red and green pigments can be deduced by examining the DNA sequences of the corresponding genes.

Needed in the art is an improved method of diagnosing vision disorders that arise as abnormalities in the cone photoreceptors.

BRIEF SUMMARY OF THE INVENTION

The present invention is a method of detecting cone-photoreceptor-based vision disorders. In one embodiment, the method comprises the steps of examining the genes encoding red and/or green cone pigments and predicting the type or extent of cone-photoreceptor-based vision disorder by correlation of a "poison" sequence with the sequence of gene or protein sequence. (Combinations that are associated with disease will be referred to as "poison" sequence combinations.)

The gene or amino acid sequence to be examined is the amino acid specified at codon positions 65, 111, and 116 in exon 2; 153, 171, 174, 178, and 180 in exon 3; 230, 233, and 236 in exon 4; and 274, 275, 277, 279, 285, 298 and 309 in exon 5 of the photopigment genes.

In a preferred form of the invention, the correlation is made to achieve a diagnosis of age related macular degeneration, red-green color vision defects, cone degeneration or B-cone monochromat disorder.

In another embodiment, the present invention is a method of detecting red-green color vision disorders and determining their relative severity. The method comprises the steps of first examining the deduced spectral separation of the visual pigments encoded by a patient's X-linked visual pigment genes and then predicting the presence and degree of vision disorder from the deduced spectral separation.

It is an object of the present invention to predict or diagnose a patient's visual disorder.

It is an advantage of the present invention that a diagnosis or prognosis of a visual disorder may be made without reliance on behavior characteristics.

Other objects, features and advantages of the present invention will become apparent after examination of the specification, claims and drawings.

BRIEF DESCRIPTION OF THE SEVERAL VIEWS OF THE DRAWINGS

The file of this patent contains at least one drawing executed in color. Copies of this patent with color drawings will be provided by the Patent and Trademark Office upon request and payment of the necessary fee.

FIG. 1 is a diagram of the general organization of the photopigment gene and spectral tuning of L pigments in deuteranomalous men. FIG. 1A is a diagram of exons 2, 3, 4, and 5 of the photopigment gene along with indications of the location of the 18 dimorphic codons. FIG. 1B is a comparison diagram of the normal red (shaded) gene and positions encoding alternative codons (clear). FIG. 1C tabulates the absorption maxima of the red pigments encoded by the diagramed gene.

FIG. 2 tabulates the analysis of the X-linked visual pigment genes in deuteranomalous men.

FIG. 6 tabulates the amino acid assignment at the 18 dimorphic sites with various protan vision disorders.

DETAILED DESCRIPTION OF THE INVENTION

Figure 3A:
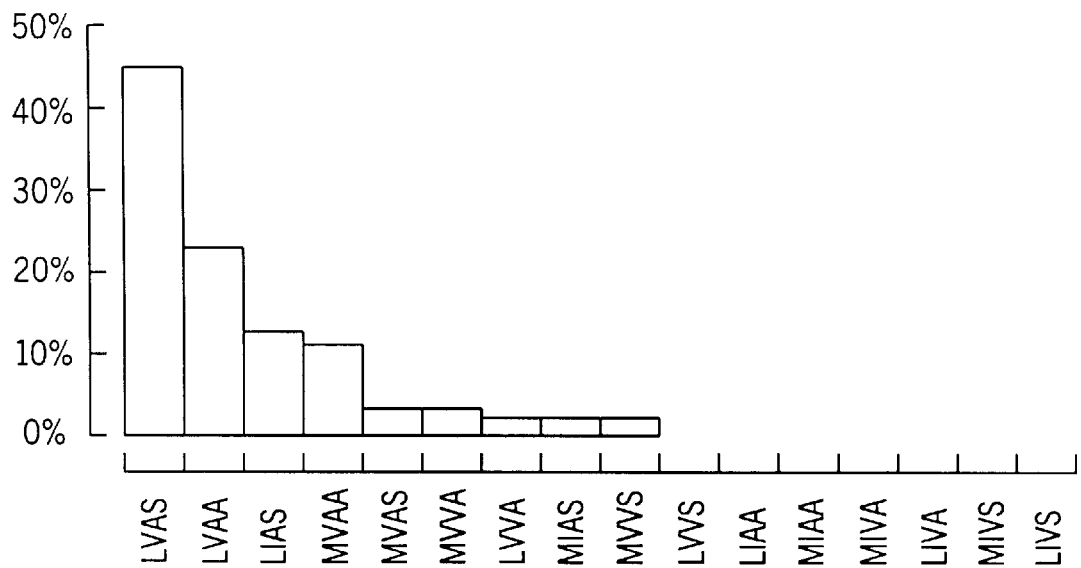
FIG. 3A and B is a histogram comparing amino acids at selected positions in the unselected population (A) and individuals with AMD (B).

The present invention provides accurate diagnosis (and in some cases prognosis) of a range of vision disorders that originate as defects of the cone photoreceptors of the eye. These disorders include both stationary and progressive eye disorders as follows: red-green color blindness (diagnosis is of the presence, the type, and the degree of the defect including the disorders deuteranopia, protanopia, protanomaly and deuteranomaly), incomplete achromatopsia, cone and cone-rod degeneration and macular degeneration including age related macular degeneration.

In one embodiment, the present invention is a method of detecting cone-photoreceptor-base vision disorders by examination of the genes encoding the red and/or green pigments (or of the proteins themselves) and predicting the type or extent of cone-photoreceptor-based vision disorder by correlation with the gene or protein sequence. In another embodiment, the present invention discloses that an examination of specific photopigment gene sites responsible for tuning photopigment absorption spectra reveals differences that predict variations in the color defect in vision disorders. The results indicate that the severity of the defect in deuteranomalous color vision depends on the degree of similarity (or "predicted spectral separation") among the residual photopigments that serve vision in the color anomalous eye.

Predicting the severity of a deficit from examination of a person's genetic make-up may prove to be particularly challenging for disorders that involve the nervous system As Table 1, below, discloses, diagnosis requires information about each of the two variables, which cones will be affected and at what life stage will the defect appear. There are 18 dimorphic codons that occur in the red-cone and green-cone pigment genes. Information about the amino acid encoded at these dimorphic sites is informative about each of the two variables among cone based vision disorders. Thus, a genetic analysis of the identities of the 18 codons in the red- and green-cone pigment genes can be diagnostic of cone based vision disorders. Information obtained from paper and pencil vision test gives information about the relative function of the red-, green-, and blue-cones. The information from the paper and pencil test augments the information from the genetic test.

TABLE 1

|  |  | STATIONARY RED-GREEN COLOR VISION DEFECT | | STATIONARY BLINDING | CONE DISTROPHY CONE-ROD | AGE |
|  |  | PROTAN Protanopla Protanomaly | DEUTAN Deuteranopia Deuteranomaly | DISORDERS Blue-cone Monochromacy | DISTROPHY MACULAR DE- GENERATION | RELATED MACULAR DEGENERATION |
| DEFECT IN RED | EARLY MIDLIFE LATE | + | | + | + + + + | + + + |
| DEFECT IN GREEN | EARLY MIDLIFE LATE | | + | + | + + + | + + + |

Defects in the red and green cones that appear at birth and cause color blindness are shared in common with other vision disorders.

and manifest themselves primarily as differences in behavior. Nonetheless, herein are examples of a class of human color vision defect in which differences among the genes predict the severity of color vision loss.

Determination of Cone-Photoreceptor-Based Vision Disorders

A. Description of the molecular genetics diagnostic portion of the test:

The diagnosis of cone-photoreceptor-based vision disorders by the method of the present invention involves the use of standard molecular biology methods, including the polymerase chain reaction (PCR), to examine the identities of all or a subset of 18 dimorphic nucleotide positions among the red and green photopigment genes. The pattern of nucleotide differences predicts the presence or absence of vision disorder. Different patterns of nucleotide identities correspond to different disorders and different degrees of severity within one class of disorder.

Mutations in the red and green cone photopigment genes can cause cone-based vision disorders including color blindness, stationary blinding disorders such as blue-cone monochromacy, and degenerative disorders including cone dystrophy, cone-rod dystrophy, macular degeneration and age related macular degeneration. The differences between these vision disorders depend on two variables. 1) Which cone type is affected, red-cones, green cones or both, and 2) at what stage in life does the defect appear. The possible life stages can be broken into three possibilities tabulated below in Table 1. Early, the defect is present at birth or shortly after; these are usually considered stationary. Mid, the defect appears in youth to middle life; these are considered to be degenerative disorders. Late, the defect appears late in life; these are degenerative disorders associated with senescence.

Therefore, the goal of the test is to determine the amino acids specified at positions 65, 111, and 116 in exon 2; 153, 171, 174, 178, and 180 in exon 3; 230, 233, and 236 in exon 4; and 274, 275, 277, 279, 285, 298, or 309 in exon 5 of the red and green cone photopigments and to look for "poison" combinations of amino acids at these positions in the diagnosis of vision disorders. One might not have to examine all 18 dimorphic positions to make a diagnosis. For example, because the dimorphic positions in exon 5 are tightly linked, one typically only has to examine one of the codon positions within exon 5 to make an initial identification of the gene as encoding either a red or green cone photopigment.

The dimorphic positions encoded in exons 2, 3, and 4 are preferably all examined. However, some disorders do not require that all positions be reviewed. Table 3, below, describes a grouping of the positions and their diagnostic potential.

Suitable vision disorders for diagnosis by the present invention include any disorder that originates in the cone photoreceptors, such as red-green color blindness (diagnosis is of the presence, the type and the degree of the defect including the disorders deuteranopia, protanopia, protanomaly, and deuteranomaly), incomplete achromatopsia, cone and cone-rod degeneration and macular degeneration, including age-related macular degeneration.

Figure 4:
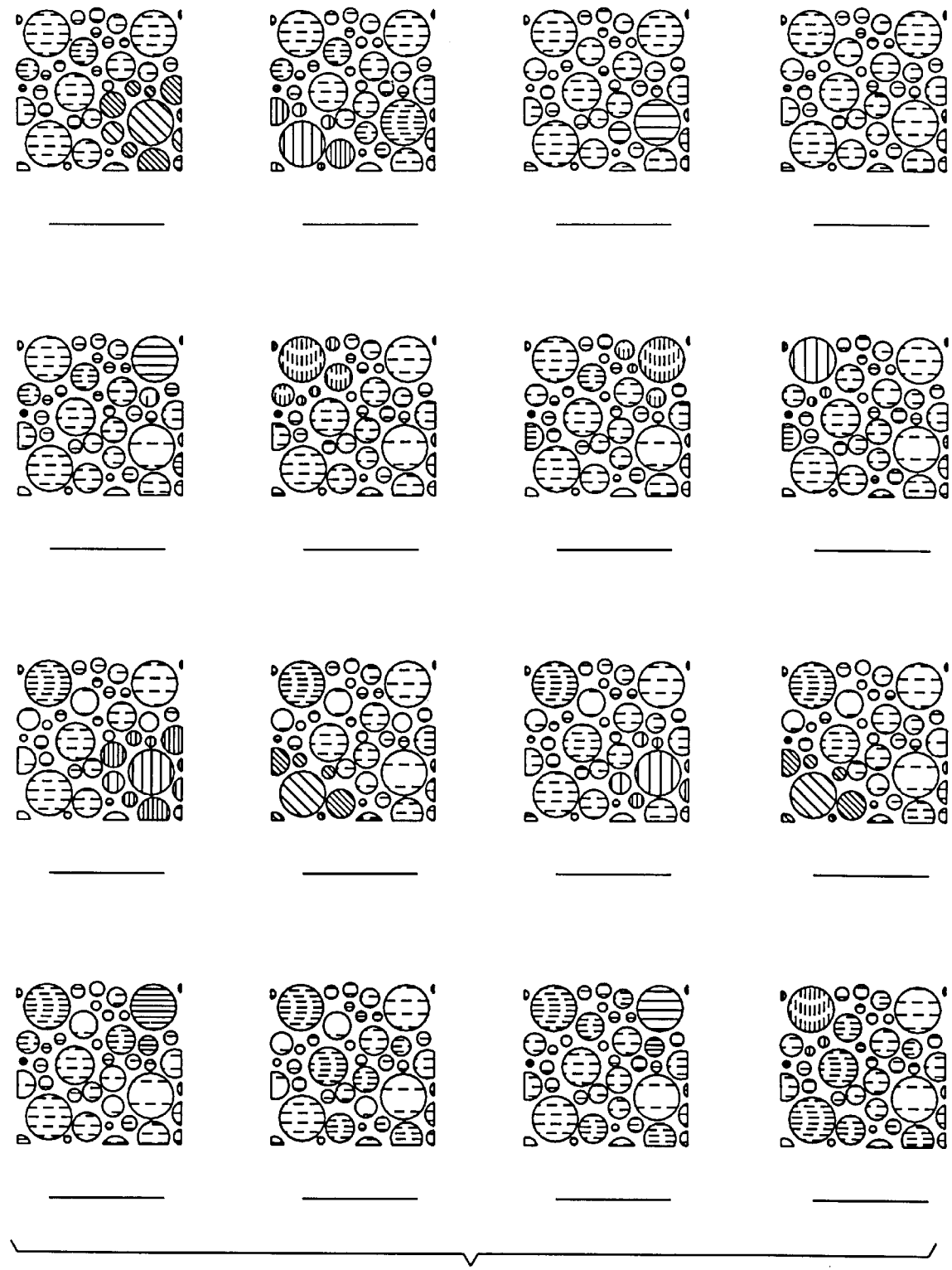
FIG. 4 is a color diagram of a paper and pencil test for color vision disorders.

A preferable approach to achieve this goal is to first assess the patient's color vision using a pencil and paper color vision test, such as that of FIG. 4, described in detail below and in the Examples. One would then preferably examine the DNA sequence of the red and/or green cone pigment genes so that the presence and identity amino acids at the above-specified codon positions can be deduced from the DNA sequence.

B. Paper and pencil color vision test

Description of the test

A preferable example of a paper and pencil color vision test is described below in the Examples. The preferred test consists of a single piece of paper which the examinee marks by hand. Instructions to the examinee are written on a separate page or they are given orally. The test is not timed, but it usual that a person would read (or hear) the instructions and take the test in a total time of less than 10 minutes.

On the test page there are several colored test patches. Each patch is a roughly square area that contains gray colored dots of varying sizes and may or may not contain a pastel (not gray) colored dot. Examinee is asked to rate the relative vividness of the color in each patch relative to other colors on the same test page.

Results to be achieved by the test

Normal daylight vision is based on the presence of three classes of light sensitive cells (called "cone photoreceptors" or "cones") in the eye. The three cone photoreceptors are sensitive to different regions of the visible spectrum. Vision disorders that affect the cones can affect either, one, two or all three classes of cones. Knowing which cone class(es) are affected and the degree of loss of function is highly informative in the diagnosis of different types of cone based vision disorders.

The test is designed to individually test the visual sensitivity of the red, green and blue cones. The test page has three different classes of stimuli. One set is designed to test blue cone function, one set tests green cone function, and one tests red cone function.

Examples of vision disorders that differentially affect the different classes of cone photoreceptors are:

1) There are two inherited forms of red-green color blindness. One is caused by absence of function of red cones and the other by absence of function of the green cones.
2) A third form of color blindness, called tritanomaly (blue-yellow color blindness) is caused by malfunction of the blue cones.
3) A blinding condition called blue-cone monochromasy is caused by lack of both green and red cone function. (Note: there are many more in this list; these are examples).

C. Molecular diagnostic methods

Figure 5:
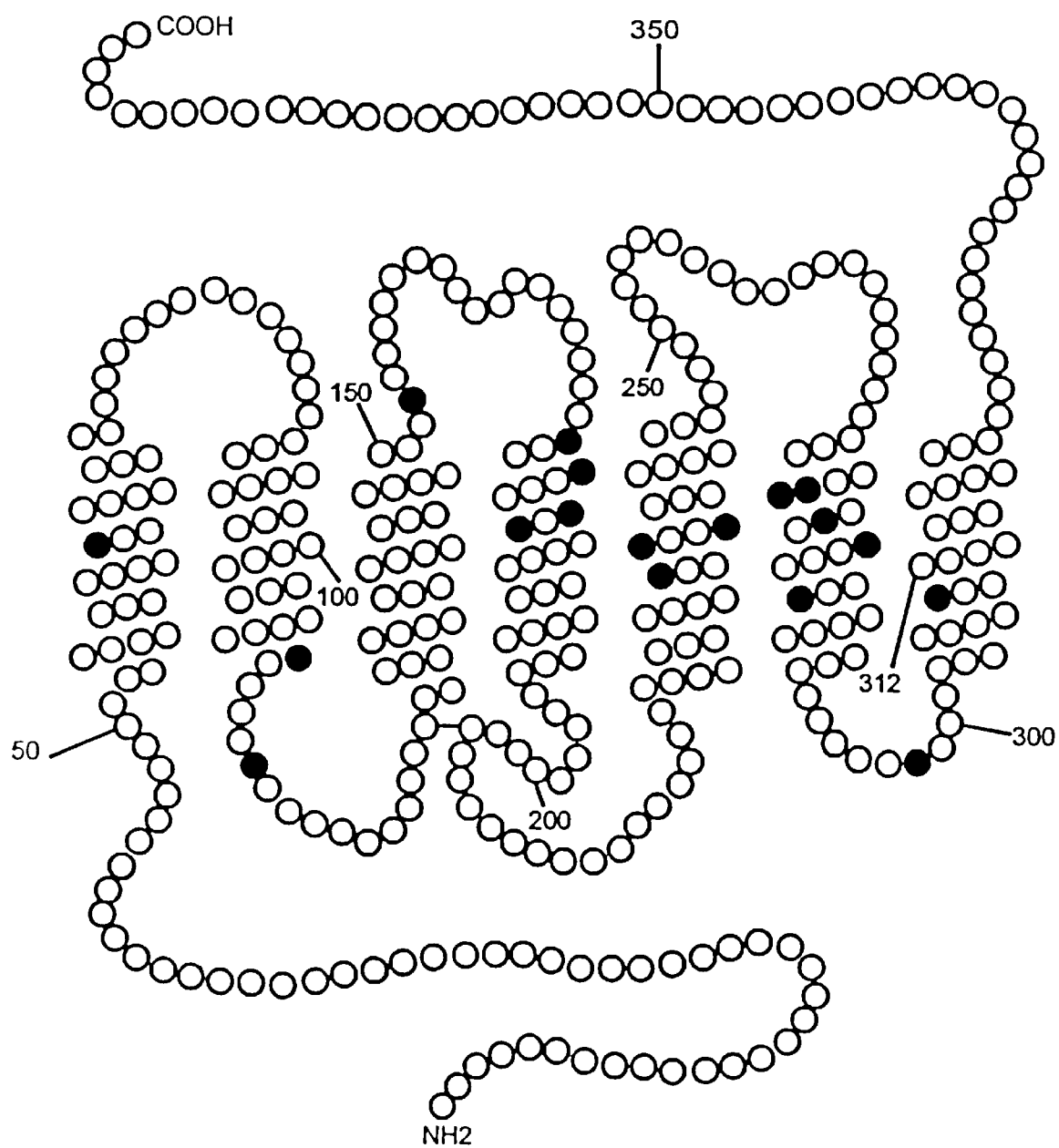
FIG. 5 is a diagram of the variant amino acid positions in a protein diagram of the human X-linked pigments.

Table 2, below, compares the dimorphic codon location and the two alternative identities of the dimorphic codon. These are the positions that one would wish to examine to evaluate the occurrence or severity of a cone-based vision disorder in a patient. FIG. 5 diagrams the positions of the variant amino acids within the pigment protein itself.

TABLE 2

| | Exon in X-chromosome cone pigment genes | Codon number | The two alternative identities of the dimorphic codon | | notes |
|---|---|---|---|---|---|
| 1 | EXON | 65 | T | I | |
| 2 | 2 | 111 | I | V | |
| 3 | | 116 | S | Y | |
| 4 | EXON | 153 | L | M | |
| 5 | 3 | 171 | I | V | |
| 6 | | 174 | A | V | |
| 7 | | 178 | I | V | |
| 8 | | 180 | S | A | |
| 9 | EXON | 230 | I | T | |
| 10 | 4 | 233 | A | S | |
| 11 | | 236 | M | V | |
| 12 | EXON | 274 | I | V | Exon 5 |
| 13 | 5 | 275 | F | L | encodes the |
| 14 | | 277 | T | F | spectral |

TABLE 2-continued

| Exon in X-chromosome cone pigment genes | Codon number | The two alternative identities of the dimorphic codon | | notes |
|---|---|---|---|---|
| 15 | 279 | V | F | difference |
| 16 | 285 | T | A | between Red |
| 17 | 298 | A | P | (left) and |
| 18 | 309 | Y | F | Green (right) |

There are currently a variety of molecular biological methods available that allow examination of the DNA sequences of the red and green photopigment genes. For example, gene fragments may be amplified using the polymerase chain reaction (PCR). The red and green pigment genes can be separately and selectively amplified as described previously (J. Neitz, M. Neitz and Grishok, *Vision Research* 35: 2395–2407, 1995).

Amplified gene fragments will preferably be subjected to one or more of the following procedures that provide information about the DNA sequence:

1) Direct DNA sequence of the PCR products as described previously (J. Neitz, M. Neitz and Grishok, supra, 1995).
2) Restriction digestion analysis (described previously in J. Neitz, M. Neitz and Grishok, supra, 1995). Some of the amino acid substitutions indicated above are accompanied by a restriction site polymorphism. For example, the amino acid at position 180 is either a serine or an alanine. If alanine is encoded, the DNA fragment contains a BsoFI restriction site that is absent if serine is the amino acid encoded. Thus, PCR-amplified DNA fragments can be digested with appropriate restriction enzyme and the digestion products will be electrophoretically separated. The sizes of the fragments may be determined. Based on the sizes of the fragments observed, information about the DNA sequence and therefore about the amino acid sequence will be deduced.
3) Single strand conformation polymorphism or other similar procedures. The amplified DNA fragment is fluorescently or radioactively end labeled, denatured into single strands, and the strands are separated electrophoretically. Based on the mobility of the strands in the electric field, information about the DNA sequence can be deduced.

Correlation of Amino Acid Sequence At Specified Positions and Vision Disorders

Once one has determined the amino acid specified at the above-described codon positions, one can then compare this amino acid data to the experimental data generated below in Examples A, B, and C. For example, Table 4, below, indicates that the amino acid combination MVAS at positions 153, 171, 174 and 180 is suggestive of age-related macular degeneration. Therefore, the particular combination of amino acids at positions 153, 171, 174, and 180 is an especially preferred diagnostic tool. Table 4, below, also discloses combinations of amino acids at positions 153, 171, 174, 178, and 180 of exon 3 as being more diagnostic of deuteranomaly, cone degeneration, or B-cone monochromat condition.

We envision that one will find other diagnostic "poison" combinations and the present invention is meant to encompass the correlation of any particular amino acid pattern within the 18 specified positions as being diagnostic of cone-photoreceptor-based vision disorders.

Flow Chart for Molecular Diagnostics Testing for Cone-Based Vision Disorders.

The following is a preferable method for molecular diagnosis of cone-based vision disorders:

Preferably, each patient will first take the paper and pencil color vision test, such as that test described below.

The molecular diagnostics tests will then be carried out on genomic DNA isolated from peripheral, whole blood or from cells from a cheek swab or other cells provided by the patient. One then asks and answers the following questions. (One should refer to Table 3, at the end of this flow chart, for a summary of molecular diagnostics testing.)

1. Does the patient have both red and green pigment genes? One must examine exon 5 of the red and green pigment genes to answer this question. Exon 5 codons 274, 275, 277, 279, 285, 298, 309 specify amino acids IFTVTAY (SEQ ID NO: 6) in red genes. Exon 5 codons 274, 275, 277, 279, 285, 298, 309 specify amino acids VLFFAPF (SEQ ID NO: 7) in green genes. As these codons are closely linked, one typically only has to determine the codon at one of these positions to be able to assign identity to the genes.

A. If the patient has red genes only—(exon 5 codons 274, 275, 277, 279, 285, 298, 309 specify amino acids IFTVTAY (SEQ ID NO: 6)): DIAGNOSTIC OF BLUE CONE MONOCHROMACY OR DEUTAN DEFECT. Paper and pencil test can discriminate between these disorders. If no paper and pencil test is available for the patient, further molecular analysis will distinguish between these.

B. How many red genes does the patient have?
  (i) One red gene only: DIAGNOSTIC OF BLUE CONE MONOCHROMASY OR DEUTERANOPIA.
    a) exon 3 codons 171, 174, 178 of red gene specify amino acids IAV. FINAL DIAGNOSIS—BLUE CONE MONOCHROMACY. Preferably, confirm with paper and pencil test.
    b) exon 3 codons 171, 174, 178, of red genes specify amino acid combinations other than IAV. FINAL DIAGNOSIS—DEUTERANOPIA.
  (ii) More than one red gene: DIAGNOSTIC OF A DEUTAN DEFECT. To determine whether deuteranopia or deuteranomaly, examine the dimorphic codons in exons 2, 3, and 4 of the genes in greater detail as follows:
    a) If there are no differences in any of the 11 codons in exons 2, 3 and 4 that are dimorphic among red pigment genes: FINAL DIAGNOSIS—DEUTERANOPIA.
    b) If there are differences in exons 2, 3 or 4: DIAGNOSTIC OF DEUTERANOMALY. How severe is the deuteranomalous defect? Examine differences in exons 2, 3 and 4 in great detail, and from this analysis determine the predicted spectral separation between the red pigments encoded by the genes.
      Differences in exons 2 and 3 but not 4, predicted spectral separation −0.6 to 3 nm. FINAL DIAGNOSIS—VERY SEVERE DEUTERANOMALY.
      Differences in exon 2 only, predicted spectral separation 1 to 4 nm. FINAL DIAGNOSIS—SEVERE DEUTERANOMALY.
      Differences in exons 2 and 4 but not 3, predicted spectral separation 5 to 7.6 nm. FINAL DIAGNOSIS—MILD DEUTERANOMALY.
      Differences in exons 2 and 3, but not 4, predicted spectral separation about 8 nm. FINAL DIAGNOSIS—MILD DEUTERANOMALY.
      Differences in exons 2, and 4 but not 3, predicted spectral separation about 9 nm. FINAL DIAGNOSIS—VERY MILD DEUTERANOMALY.
      Differences in exons 2, 3 and 4, predicted spectral separation about 12 nm. FINAL DIAGNOSIS—VERY MILD DEUTERANOMALY.

C. Patient has green genes only (exon 5 codons 274, 275, 277, 279, 285, 298, 309 specify amino acids VLFFAPF (SEQ ID NO: 7)). DIAGNOSTIC OF A PROTAN DEFECT.

D. How many green pigment genes does the patient have?
  (i) Only one green gene: DIAGNOSTIC OF A PROTAN DEFECT, MAY BE ACCOMPANIED BY MID-LIFE ONSET OF RETINAL DEGENERATIVE DISORDER.
    a) exon 3 codons 153, 171, 174, 178 and 180 in green gene specify the amino acids LVAVA (SEQ ID NO: 8). FINAL DIAGNOSIS—PROTANOPIA, WITH high risk for developing CONE-ROD DYSTROPHY OR CONE DYSTROPHY.
    b) exon 3 codons 153, 171, 174, and 180 in green gene specify the amino acids LVAS (SEQ ID NO: 9). FINAL DIAGNOSIS—PROTANOPIA.
  (ii) More than one green gene. DIAGNOSTIC OF A PROTAN DEFECT, MAY OR MAY NOT BE ACCOMPANIED BY MID-LIFE ONSET OF RETINAL DEGENERATIVE DISORDER. To distinguish between protanopia and protanomaly, molecular analysis of the green genes is necessary. Examine gene sequences in exons 2, 3 and 4 in detail.
    a) no differences among the green pigment genes, and exon 3 codons 153, 171, 174 and 180 specifies the amino acids LVAVA (SEQ ID NO: 10). FINAL DIAGNOSIS—PROTANOPIA ACCOMPANIED BY CONE-ROD DYSTROPHY OR CONE DYSTROPHY.
    b) no differences among the green pigment genes, and exon 3 codons of the green pigment genes do not specify amino acids LVAVA (SEQ ID NO: 10). FINAL DIAGNOSIS—PROTANOPIA.
    c) differences among the green pigment genes in exon 2 only, specifically at codon 65. Exon 3 of the green pigment genes do not differ, or do differ and the first gene in the array specifies LVAVA (SEQ ID NO: 10) at codons 153, 171, 174, and 178. FINAL DIAGNOSIS—PROTANOMALY ACCOMPANIED BY CONE-ROD DYSTROPHY OR CONE DYSTROPHY.
    d) differences among the green pigment genes in exon 2 only, specifically at codon 65. Exon 3 of the green pigment genes do not differ, or do differ BUT the first gene in the array DOES NOT specify LVAVA (SEQ ID NO: 10) at codons 153, 171, 174, and 178: FINAL DIAGNOSIS—PROTANOMALY.
    e) differences among the green pigment genes in exon 3 only, and specifically at codon 180, codons 153, 171, 174, 178 and 180 do not specify LVAVA (SEQ ID NO: 10): FINAL DIAGNOSIS—PROTANOMALY.
    f) differences among the green pigment genes in exon 4. Final Diagnosis-Protanomaly E. Patient has both red and green pigment genes, as determined by examining exon 5 of the genes. This occurs both in people with normal color vision, as well as in people with deutan defects and in people with blue cone monochromacy. It is much more rare in people with protan defects. Does the patient have a red-green color vision defect? The pencil and paper color vision test can be used to determine this. If the test is unavailable initially, molecular diagnostics can be done to determine whether the person has a red-green color vision defect.

(i) What is the number of red and green genes?

(ii) Patient has 1 red and 1 green pigment gene. DIAGNOSTIC OF NORMAL COLOR VISION OR A DEUTAN DEFECT. To distinguish between these possibilities, examine the green pigment genes. Individuals with Deutan defects often have "poison" sequence combinations in their green pigments. Examine the gene sequences in exon 3 of the green genes to determine the amino acids specified by codons 153, 171, 174, 178 and 180 in exon 3, and at codons 230, 233, and 236 in exon 4.

a) Poison amino acid combinations, i.e., those other than the normal MVAIATSV, MVVVATSV, LVAIATSV, LVAISTSV (SEQ ID NOs: 11, 12, 13, and 14). Examples of abnormal sequences are MVAIAIAM, LIAISTSV, MVAISTSV, or MVVIATSV (SEQ ID NOs: 15, 16, 17, and 18) encoded by exons 3 and 4 of green genes at codons 153, 171, 174, 178, 180, 230, 233 and 236. FINAL DIAGNOSIS—DEUTERANOPIA. PREFERABLY CONFIRM WITH PAPER AND PENCIL TEST.

b) Non-poisonous amino acid combinations at codons 153, 171, 174, 178, 180, 230, 233 and 236. (MVAIATSV, MVVVATSV, LVAIATSV, LVAISTSV, SEQ ID NOs: 11, 12, 13, and 14). FINAL DIAGNOSIS—NORMAL COLOR VISION.

(iii) Patient has more green pigment genes than red pigment genes. FINAL DIAGNOSIS—NORMAL COLOR VISION. MUST CONFIRM WITH PAPER AND PENCIL TEST.

(iv) Patient has more red pigment genes than green pigment genes. DIAGNOSIS—DEUTAN DEFECT. Must confirm with the pencil and paper test. To make the FINAL DIAGNOSIS with regard to whether the patient has deuteranopia versus deuteranomaly, and to determine the degree of severity of the deuteranomalous defect, complete the analysis of the red pigment genes as described above. That is, determine the differences in the sequences between the red genes and determine the predicted spectral separation between the encoded red pigments.

2. Diagnosing patients at risk for developing age related macular degeneration

A. Examine first (most 5') cone pigment gene in the X-chromosome array. Confirm that it is a R-cone pigment gene by examine sequences of exon 5.

B. Examine for Non-poisonous amino acid combinations at codons 153, 171, 174, 178, 180, 230, 233 and 236. Sequences other than MVAIATSV, MVVVATSV, LVAIATSV, LVAISTSV (SEQ ID NOs: 11, 12, 13, and 14) indicate a risk for developing AMD. Red-green color vision deficiency shown by paper and pencil color vision test would be indicative of AMD.

TABLE 3

| | STATIONARY RED-GREEN COLOR VISION DEFECT | | STATIONARY BLINDING | CONE DISTROPHY CONE-ROD | AGE |
|---|---|---|---|---|---|
| | PROTAN Protanopia protanomaly | DEUTRAN deuteranopia deuteranomaly | DISORDERS Blue-cone Monochromasy | DISTROPHY MACULAR DEGENERATION | RELATED MACULAR DEGENERATION |
| Exon 2 Codons 65, 111, 116 | + Diagnosis of severity | + Diagnosis of severity | | | |
| Exon 3 Codons 153, 171, 174, 178, 180 | + Severity and presence | + Severity and presence | + | + | + |
| Exon 4 Codons 230, 233, 236 | + Severity and presence | + Severity and presence | + | + | |
| Exon 5 Codons 274, 275, 277, 279, 285, 298, 309 | + Presence | + Presence | + Presence | + Use to tell if abnormal sequence in other exon occurs in R- or G-cone | + Use to tell if abnormal sequence in other exon occurs in R- or G-cone |

+codons in that exon can be used in diagnosis of corresponding disorder

Red-Green Color Blindness

In another embodiment, the present invention is a method of specifically detecting red-green vision disorders. The method comprises the steps of first examining the predicted spectral separation of red and green pigments encoded by a patient's X-linked visual pigment genes, preferably as described above, and then correlating the spectral separation with a degree of vision disorder.

Rearrangements of the visual pigment genes are associated with defective color vision and with differences between types of red-green color blindness. A characteristic feature of the most common category of defective color vision, deuteranomaly, is a large variation in the severity of the loss of color vision.

Deuteranomaly is the most common inherited color vision defect, affecting more than 1 in every 20 men in the United States. The condition arises from the absence of one of the cone photopigments, the normal pigment sensitive to middle wavelengths (green pigment). Even though deuteranomalous individuals are missing normal green photopigment function they retain varying degrees of trichromatic color vision which is based on a short wavelength sensitive pigment plus two more closely separated photopigments which absorb in the long wavelength (L) region of the spectrum.

Results from Southern analysis have revealed that the pigment gene arrangements of deuteranomalous men are different from those of most men with normal color vision (J. Nathans, et al., Science 232: 193, 1986; J. Nathans, et al., Science 232: 203, 1986; S. S. Deeb, et al., Am. J. Hum. Genet. 51: 687, 1992). However, even though deuteranomals vary in the numbers and ratios of their M and L cone pigment genes, as do normals (J. Nathans, et al., supra, 1986; J. Nathans, et al., supra, 1986; M. Neitz and J. Neitz, Science 267: 1013, 1995), the genetic differences failed to correlate with the extent of color vision defect.

In people with normal color vision, the capacity to distinguish colors in the red-to-green region of the spectrum is based on the difference between the M and L cone pigments. In contrast, the color vision of the deuteranomalous is based on two more closely separated pigments (J. Neitz and M. Neitz, in *Molecular Genetics of Inherited Eye Disorders* A. S. Wright, B. Jay, Eds., Harwood Academic Publishers, Chur, 1994; J. Pokorny and V. C. Smith, *J. Opt. Soc. Am.* 67: 1196, 1977; *Color Res. Appl.* 7: 159, 1982; P. DeMarco, et al., *J. Opt. Soc. Am.* A 9: 1465, 1992; T. P. Piantanida, *Am. J. Optom. & Physiol. Optics* 53: 647, 1976; J. Pokorny and V. C. Smith, in *Frontiers of visual science: Proceedings of the 1985 symposium* Committee on Vision, Ed., National Academy Press, Washington, D.C., pp. 150, 1987. One hypothesis proposed to explain the differences in color vision among deuteranomals is that individuals differ in the spectral separation of their remaining X-encoded pigments. A deuteranomal who has well-separated pigments would have better color vision, whereas one whose pigments are more similar would have poorer color vision. This idea has been called the "spectral proximity hypothesis" (Regan, et al., *Vision Res.*, 34: 1279, 1994).

In the study described below in the Examples, 16 young men were identified as deuteranomalous from a standard color matching test for red-green color vision defects, the Rayleigh match. In this test, the subject is asked to mix together a red and green light in a proportion that exactly matches the appearance of a monochromatic yellow light, as has been described (J. Neitz and G. H. Jacobs, *Nature* 323: 623, 1986; *Vision Res.* 30: 621, 1990). Deuteranomalous subjects choose a much higher proportion of green light in the mixture than a person with normal color vision. This color matching test also distinguishes deuteranomalous trichromats from dichromats (as was done in M. Neitz, et al., *Vision Res.* 35: 2095, 1995), who have only two cone photopigments and thus suffer the most severe of the common red-green color defects.

Once deuteranomalous subjects were differentiated from men with normal color vision and from dichromats using the Rayleigh match, we assayed the severity of the color vision impairment using the American Optical, Hardy, Rand and Rittler (AO-HRR) pseudoisochromatic plates for color vision testing. From the complete set of plates included in the test, we used a series of six test figures designed for grading deutan color defects. (Each design in this sequence is composed of a reddish colored symbol on a background of gray dots. Each symbol in the progression is more intensely colored than the last.)

The deuteranomalous participants varied enormously in their performance on this test. Although all 16 subjects had been classified as deuteranomalous in the color matching test, it is striking that a subset of these participants nonetheless behaved normally in the everyday tasks of recognizing, naming, and sorting colors. This subgroup reported that they had no indication of a color vision abnormality prior to being identified as "color deficient" by formal color vision testing. When given the plate test, individuals in this group were challenged only by the most difficult plate (plate 1 of the AO-HRR test), a plate that some people with normal color vision also fail to interpret correctly. In contrast to the least affected men, the most extreme case (subject 189) was unable to detect any of the symbols, even the one with the largest color difference from its background. The symbol, an "X" in that design, appears as red to those with normal color vision but it was invisible amongst the gray dots to subject 189.

The Examples below demonstrate that the extent of the color vision defect can be expressed numerically as the distance (D) in color space that must differentiate the symbol on the plate from its background before the person can interpret it correctly. (The degree of color vision defect can be expressed quantitatively from measurements of the colors in the designs as specified by their coordinates, in this case in units of the CIE u'v' diagram (following B. C. Regan, et al., *Vision Res.* 34: 1279, 1994). For normal color vision this represents an approximation of a two-dimensional color diagram in which equal distances in different locations correspond to equal perceptual differences.

Thus, the extent of the defect can be expressed numerically as the distance (D) in the color diagram that must differentiate the symbol from its background before the person can interpret it correctly. Lower D values indicate better color vision; the men categorized as having "very mild" defects were able to read the plate with D=0.022. Higher D values indicate poorer color vision; subject 189 was assigned D>0.081 because he was unable to interpret even the most vivid plate.

Southern analysis of the pigment genes of our 16 participants showed no correlation with differing degrees of color vision defect (see FIG. 2). It is noteworthy that most of the deuteranomalous men had apparently complete M pigment genes. These are indicated by the clear arrows. The reason M pigments do not contribute to deuteranomalous color vision is not understood.

A molecular genetic test of the spectral proximity hypothesis requires information about the amino acids that control the spectral sensitivities of the X-encoded visual pigments, information that is now available (M. Neitz, et al., supra, 1995; J. Neitz, et al., *Nature* 342: 679, 1989; M. Neitz, et al., *Science* 252: 971, 1991; T. Chan, et al., *J. Biol. Chem.* 267: 9478, 1992; A. J. Williams, et al., *EMBO Journal* 11: 2039, 1992; S. L. Merbs and J. Nathans, *Science* 258: 464, 1992; A. B. Asenjo, et al., *Neuron* 12: 1131, 1994). All spectral differences are encoded by exons 2 to 5. The largest spectral shifts are encoded by changes in exon 5 which divide the X-encoded pigments into two major classes, M and L (J.

Neitz and M. Neitz, supra, 1994; M. Neitz, et al., supra, 1991). Exons 2, 3 and 4 each encode changes which produce relatively smaller spectral shifts, making them candidates for controlling spectral differences among the pigments in deuteranomals.

In the method of the present invention, one would calculate the spectral separation of the patient's L and M genes, preferably as described in the Examples and in the flowchart above and correlate this separation with the severity of vision disorder. FIG. 2, below, correlates the predicted spectral separation with the severity of vision disorder in our experimental subject. In general, a predicted spectral separation of greater than 8 nm is predictive of a very mild red-green color blindness disorder, a separation of 5 nm–8 nm is predictive of a mild vision disorder, a separation of 1 nm–4 nm is predictive of a severe disorder, and a separation of less than 1 nm is predictive of a very severe disorder. (For the context of this paragraph, the predicted spectral separation will be the average number calculated by the method of Merbs, et al, *Science* 258, 464 (1992) and Asengo, et al, *Neuron* 12, 1131 (1994). Both of these documents are herein incorporated by Reference.

In order to obtain the spectral separation data, DNA is preferably derived from a tiny drop of the patient's blood or from cheek cells collected with swabs. One then examines, as described above, the dimorphic codon positions.

A paper and pencil type color vision test is also preferably administered. Most preferably, the test described in the Examples is administered. Results from the paper and pencil test are used to augment the genetic information in making the diagnosis.

EXAMPLES

A. Red-Green Color Blindness

The genes of the 16 deuteranomalous participants were studied by performing long-PCR and then examining the products by restriction analysis and by direct sequencing to analyze the X-linked pigment gene array of each man. We then constructed a model of the pigment gene arrangement for each person which was used to predict the largest spectral separation among his L-pigments. On the basis of color vision behavior, participants segregated into five different levels of deutan color vision defect ranging from dichromatic to nearly normal.

Spectral tuning studies suggest that amino acid differences encoded by exons 2, 3 and 4 of the photopigment genes are most likely responsible for the spectral separation between the X-encoded pigments underlying deuteranomaly. (Neitz, et al, *Science* 252: 971, 1991)

The spectral proximity hypothesis, supported by our results, predicts that the presence of the active differences in all three exons would be required to have the largest spectral separation and therefore the best deuteranomalous color vision. The presence of relatively fewer active differences would predict poorer color vision. Most of the participants who were least affected (very mild) had differences in all three exons. Those who were the second least affected (mild) had differences in exon 2 plus differences in either exon 3 or 4, but not both. The severely affected subjects had differences in exon 2 but neither exons 3 nor 4. Those people were distinguished from the dichromats who were identified as having a single gene sequence.

A few cases did not follow this trend but were nonetheless predicted from the DNA sequences. For example, subject 182, has quite good color vision but he has differences in the same set of exons as subjects 191, 185 and 027, who have poorer color vision. This is explained by the observation (A. B. Asengjo, et al., supra, 1994), that differences encoded by exons 2 and 4 have a larger effect when they occur in pigments with $ser^{180}$ (like subject 182) than when the pigments share $ala^{180}$. The general correspondence between the spectral separation predicted from the genes and severity of vision defect supports the spectral proximity hypothesis.

The spectral proximity hypothesis has often been challenged and alternate hypotheses proposed. For example, differences in severity of color vision defects have been suggested to derive from variation in amount of pigment produced (J. Pokorny an V. C. Smith, supra, 1987; A. L. Nagy, *J. Opt. Soc. Am.* 72: 571, 1982), or in the stability, quantum efficiency or signaling of the pigment molecule (B. C. Regan, et al., supra, 1994), or some neural factor that controls the chromatic signal at a level beyond the photoreceptors (D. Jameson and L. M. Hurvich, *J. Opt. Soc. Am.* 46: 1075, 1956).

The original version of the spectral proximity hypothesis failed to reliably predict behavior, not because the concept was wrong, but rather because it wrongly assumed that there was a fixed L pigment common to all normals and deuteranomals alike (An exception, however, is a model, progressive for its time, forwarded by M. Alpern and J. Moeller who proposed variation in normal L pigments *J. Physiol.* (London) 266: 647, 1977).

In truth, we have found that relative shifts among the pigments are what account for differences in behavior. For example, subject 189 had the poorest color vision of all the deuteranomals, yet he has differences in both exons 2 and 3, as does subject 028, a person with only a mild defect (see FIG. 2). Subject 028 segregates the functional changes between two genes so that the sequences which specify spectral shifts toward the red are assembled into one gene and those which shift it toward the green are in another gene. These yield pigments with a spectral separation of about 8 nm. In contrast, subject 189 has the long wave, redward-shifting exon 2 in his first gene but pairs it with the green-shifting exon 3. The long wave exon 3 is in his downstream genes. The pigments produced by this gene combination are closely separated in spectral sensitivity, hence his very poor color vision.

FIG. 1 is a diagram of the organization of the photopigment gene in general and of spectral tuning of L pigments in deuteranomalous men. FIG. 1A is a diagram of exons 2, 3, 4, and 5 of the photopigment gene along with indications of the 18 dimorphic codons. Referring to FIG. 1A and 1B, the majority of the spectral difference between L and M pigments is specified by exon 5. Exons 2–4 encode amino acid substitutions that produce relatively smaller spectral shifts among the L pigments. In the diagrams of the genes (arrows in FIGS. 1B and 1C) except where specifically noted, shaded areas indicate codons specifying the amino acids: Exon 2: threonine (T) 65, isoleucine (I) 111, serine (S) 116; exon 3: serine (S) 180; exon 4: isoleucine (I) 230, alanine (A) 233. Clear areas indicate: exon 2: isoleucine(I) 65, valine (V) 111, tyrosine (Y) 116; exon 3: alanine (A) 180; exon 4: threonine (T) 230, serine (S). The shaded arrowheads indicate that each gene encodes an L pigment. To predict spectral separation of the pigments in deuteranomals the table shown in FIG. 1C was used. The absorption maxima (λmax) of the L pigments encoded by the diagrammed genes were measured in vitro by the methods of S. L. Merbs and J. Nathans, *Science* 258: 464, 1992 or A. B. Asenjo, *Neuron* 12: 1131, 1994. (Both of these articles are incorporated by reference as if fully set forth herein.)

FIG. 2 tabulates the analysis of the X-linked visual pigment genes in deuteranomalous men. Referring to FIG. 2, the leftmost column shows the gene arrangements as deduced from Southern analysis (following J. Nathans, et al., supra, 1986), the number of M/L hybrid genes, and M pigment genes are indicated by a subscript number or "in" if the number was not determined.

Southern analysis does not give information about the fine structure of the genes. In the present experiments, the one, most upstream gene (first gene) and the downstream hybrid M/L pigment genes were analyzed separately.

The Expand Long Template PCR System (Boehringer Mannheim) was used exactly as recommended by the manufacturer to do long-PCR. The first gene in the array was amplified in long PCR using primers 5' GAGGCGAGGC-TACGGAGT (SEQ ID NO: 1) and 5' ACGGTATTTTGAT-GTGGATCTGCT (SEQ ID NO: 2) which correspond to sequences 862 base pairs (bp) upstream of the first exon of the first gene (Y. Wang, et al., Neuron 9: 429, 1992) and to the 3' end of intron 5 (M. Neitz and J. Neitz, supra, 1995), respectively. The PCR product served as template to amplify exons 2, 3, 4 and 5 as described previously (M. Neitz, et al., supra, 1990; M. Neitz and J. Neitz, supra, 1995; M. Neitz, et al., *Vision Res.* 35: 2395, 1995).

Restriction analysis was done on exons 3, 4 and 5 from the first gene and on exons 3 and 4 from downstream L genes. The presence of a RsaI site in exon 5 from the first gene from each male identified it as a L pigment gene (M. Neitz and J. Neitz, supra, 1995). Whether exon 3 contains an BsoFI restriction site or not indicates whether codon 180 specifies alanine or serine, respectively (M. Neitz, et al., supra, 1995). A DdeI site is found in exon 4 only when serine in specified by codon 233 and this was used to deduce whether the first gene or the downstream L genes were M4L5 hybrids. The results of the restriction analyses were confirmed by direct sequence analysis (M. Neitz, et al., supra, 1995) which was also used to determine whether the sequence of exon 2 differed among the L pigment genes in individual men.

The deduced structures of the first gene and downstream hybrid M/L pigment genes are shown (gene arrangements, this study). Except for the first gene, shown placed at the left end of each array, which was always observed to have an L gene exon 5, the relative order of the genes is not known.

Exons 2, 3 and 4 were examined to determine whether the first gene and the downstream hybrid M/L pigment genes differ at sequences in exons 2, 3 and 4 that encode spectrally active amino acid loci.

We have included the results from two dichromats (deuteranopes) from a previous study (M. Neitz, supra, 1995) for comparison with the deuteranomals.

The spectral separation values given are the largest possible for the L and M/L pigment combinations each male could have based on the deduced gene structures. Subjects 017 and 190 would be predicted to have a spectral separation of 9 nm if they expressed only the fusion gene that is least different from the first gene in the array. This would not substantially change their predicted behavior. The worst case for subject 028 would predict a 3.7–4.0 nm spectral separation and poorer color vision than he exhibits.

Spectral separations were calculated using the Xmax values measured in vitro (values from Merbs, et al., supra, 1992 are indicated by †, by Asenjo, et al., supra, 1994 by ‡) shown in FIG. 1.

B. Examples of "poison combinations" underlying other diseases.

i) Age Related Macular Degeneration (AMD or ARMD)

To evaluate the likelihood that specific amino acid combinations in the red and green cone pigments serve as a risk factor or potential cause of age related macular degeneration we conducted a pilot study by examining the red and green cone pigment gene sequences for a highly polymorphic region of exon 3. In the AMD patients, we looked only at the sequence of the red pigment genes and the experiments were done essentially as described in Neitz, Neitz, and Grishok, supra, 1995. We also looked at the red pigment gene sequences in exon 3 for a group of control individuals. The control patients represent an unselected population and none exhibit signs of the disease. However, it is a given that some fraction of the control patients will go on to develop the disease later in life.

Our rationale for looking at red pigment gene in preliminary study was as follows: In the eye, the number of red cones outnumber the green cones by about 2:1. In experiments we have done to look at the amount of red versus green pigment gene expression, we also find that there is about two to three times as much messenger RNA from red genes than from green genes. If a "poison" sequence is causing a retinal degeneration, the effect is likely to be the most pronounced if it is the gene that is expressed at a relatively high level.

Our findings were as follows: Analysis of the control patients have allowed us to define "usual" and "unusual" combinations of amino acids encoded by polymorphic positions in exon 3 of the red pigment genes. We then compared the combinations of amino acids at these same positions in the red pigments from patients with AMD and found that there is a high frequency of combinations found in AMD patients that are not found very frequently in the control population.

Referring to Table 4 below, we identified the 16 possible combinations of amino acids at 4 of the dimorphic positions specified by exon 3. This is the first column and begins with LVAS. This labeling scheme is the single letter amino acid code. We analyzed the combinations of amino acids at positions 153, 171, 174 and 180. So for example, LVAS means the person had Leucine at position 153, Valine at position 171, Alanine at position 174 and Serine at position 180.

TABLE 4

| Amino Acid Combinations | | Unselected Population | | AMD |
|---|---|---|---|---|
| LVAS | 1 | 45% | 1 | 17% |
| LVAA | 2 | 23% | 2 | 8% |
| LIAS | 3 | 12% | 3 | 25% |
| MVAA | 4 | 11% | 4 | 17% |
| MVAS | 5 | 3% | 5 | 17% |
| MVVA | 6 | 3% | 6 | 0% |
| LVVA | 7 | 1% | 7 | 0% |
| MIAS | 8 | 1% | 8 | 0% |
| MVVS | 9 | 1% | 9 | 0% |
| LVVS | 10 | 0% | 10 | 0% |
| LIAA | 11 | 0% | 11 | 0% |
| MIAA | 12 | 0% | 12 | 0% |
| MIVA | 13 | 0% | 13 | 0% |
| LIVA | 14 | 0% | 14 | 0% |
| MIVS | 15 | 0% | 15 | 0% |
| LIVS | 16 | 0% | 16 | 0% |
| | | Probability Of An Unusual Combo 32% | | Probability Of An Unusual Combo 75% |

Figure 3B:
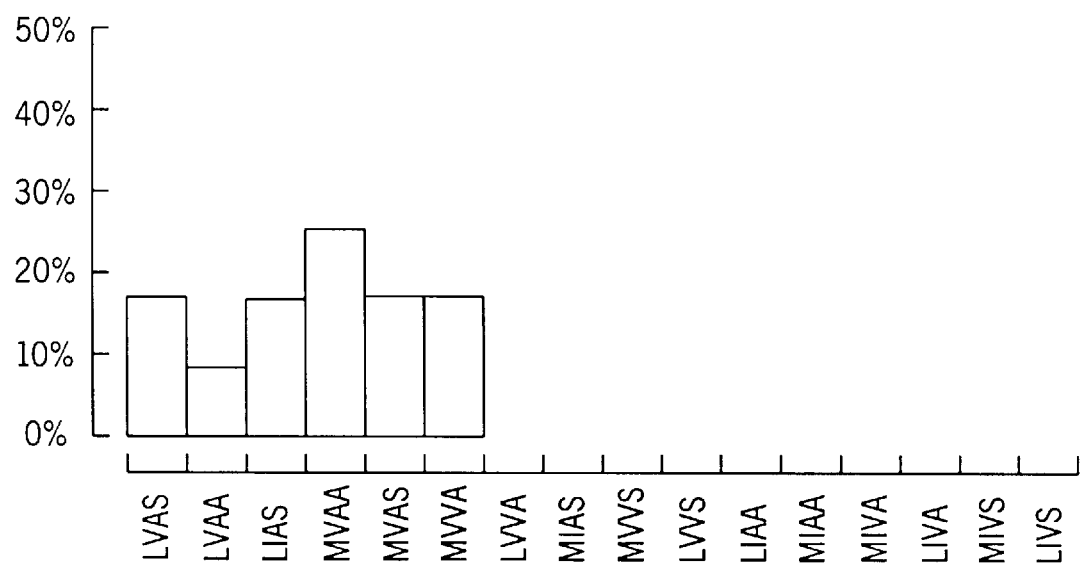

The second and fourth columns give the number assigned to each amino acid combination. Referring to FIG. 3, in the histogram, this number is plotted on the X-axis. The number is assigned based on the assumption that there was a primordial red sequence and a primordial green sequence which also correspond to the most "usual" or highest frequency sequences in the normal population. To generate other combinations besides the primordial ones requires genetic recombination between primordial red and green. The number assigned to each combination is done in a specific order such that 1 is assigned to the presumed primordial red sequence and is thus the one that is expected to occur at the highest frequency in the unselected population. The number 16 is assigned to the sequence that requires the most recombinations between the primordial red and green, and is the one expected to occur at the lowest frequency in the unselected population. The numbers between 1 and 16 follow this trend. As the assigned number increases it indicates that more recombinations between primordial red and green are required to produce a given combination, and the expected frequency of that combination in the unselected population drops.

The third column indicates the frequency of each combination in the control population (unselected with regard to age—some might go on to develop age-related macular degeneration).

The fifth column indicates the frequency of the given amino acid combination among the patients with age-related macular degeneration.

One can note that the distribution in the control population (top histogram) versus the population of people with age-related macular dystrophy (lower histogram) is quite different. Eleven of the AMD patients in this pilot study were recruited from the retina service in the department of Ophthalmology at the Medical College of Wisconsin. The other 5 AMD patients are people who died and donated their eyes to the Wisconsin Lions Eye Bank.

The difference in the distributions of the amino acid combinations in the control versus AMD populations is statistically significant (Fisher's exact test gives a P value of 0.0086).

ii) Green Pigment Genes in Deuteranomalous Men

The results for the following series of examples are tabulated in Table 5.

TABLE 5

| Amino Acid Combination Exon 3 | | | | | | | Vision‡ Disorder | (genomic sequences) Cone | B-cone |
|---|---|---|---|---|---|---|---|---|---|
| 153 | 171 | 174 | 178 | 180 | 4 | Stable Expression (mRNA) | Deuteranotmaly | degeneration | monochromat |
| M | V | A | I | A | M4 M4 | 11 | 12 | 0 | 0 |
| M | V | V | V | A | M4 M4 | 9 | 2 | 0 | 0 |
| L | V | A | I | A | | 8 | 0 | 0 | 0 |
| L | V | A | I | S | | 2 | 0 | 0 | 0 |
| Sum HIGH Frequency | | | | | | 30 | 14 | 0 | 0 | TOTAL |
| combinations | | | | | TOTAL | 30 | | | | 14 |
| M | V | A | I | A | L4 M4 | 0 | 1 | 0 | 0 |
| L | I | A | I | S | M4 M4 | 0 | 1 | 0 | 0 |
| M | V | A | I | S | M4 L4 | 0 | 2 | 0 | 0 |
| M | V | V | I | A | L4 | 0 | 1 | 0 | 0 |
| L | V | A | V | A | | 0 | 0 | 1 | 0 |
| — | I | A | V | S | | 0 | 0 | 0 | 1* |
| L | I | A | V | A | | 0 | 0 | 2* | 0 |
| Sum LOW Frequency | | | | | | 0 | 5 | 3 | 1 |
| combinations | | | | | TOTAL | 0 | | | | 9 |

‡With unknown cause
*Not included in statistical analysis. These are L-pigment genes and thus cannot be appropriately compared to the M-pigment genes in the rest of the analysis. A statistical analysis (using Fisher's exact test) that excluded these 3 subjects indicates the probability that association between low frequency sequences and vision disorder could be attributed to chance (p = 0.002). The L-pigment combinations were not found in any of 109 L-pigment genes. A separate statistical analysis (Fisher's exact test) indicates the probability of drawing these 3 abnormal pigment genes by chance (p < 0.0001).

Men with the red-green color vision defect deuteranomaly often have genes encoding green cone pigment. However, they do not have functional green cones. What is wrong the green pigment? To test the idea that in some deuteranomalous men, the green cones are non-functional because of "poison" amino acid combinations in the green cone pigment we sequenced exon 3 from the green pigment genes in a group of 19 men with deuteranomaly.

The green pigment genes were selectively amplified using the polymerase chain reaction, and the PCR products were subjected to direct DNA sequence analysis as described previously (Neitz, Neitz, and Grishok, supra, 1995). We looked at the green pigment gene sequences in deuteranomalous men versus the green pigment gene sequences expressed in eyes obtained through the Wisconsin Lions Eye Bank. The rationale of this is that the green pigment genes expressed in donor eyes did not kill the photoreceptor cells and therefore these sequences represent a control population of stably expressed, "normal" green pigment genes. The deuteranomalous green pigment genes represent a population of abnormal or nonexpressed green pigment genes.

Our findings were as follows: In Table 5 the amino acid combinations specified by exon 3 of the green pigment genes is in the leftmost column. In the next column are the number of donor eyes that express green pigment genes that specify the indicated amino acid combinations. In the series of columns called Vision Disorder, one column, labeled deuteranomaly, gives the number of deuteranomalous men whose green pigments have the specified amino acid combination. From this we see that 14 of the deuteranomalous men have "normal" amino acid combinations specified in the green pigment genes. However, 5 of the men have sequences in there green pigments that are never seen in the "normal" population. The correlation between the occurrence of these "low" frequency or "poison" amino acid combinations in the green pigments and the disease deuteranomaly are statistically significant (p=0.002 Fishers exact test) The presence of these "poison" sequence combinations in the green pigments of men are diagnostic of a specific color vision defect.

iii) Cone-degenerations (Includes cone-rod dystrophy and achromatopsia).

We have looked for the occurrence of "poison" amino acid combinations in the red and green photopigment genes from patients with cone-based retinal degenerations. Two of the patients had cone-rod dystrophy, and one had achromatopsia. All three patients had amino acid combinations specified in their red or green pigments that have never been seen in the normal populations. In Table 2, the amino acid combinations observed for these patients is indicated in the column labeled Cone degeneration. There is a highly statistically significant correlation between the "unusual" amino acid combinations observed for these three subjects and their disease. That is, the probability that there is no relationship between the disease and these unusual amino acid combinations in these three patients is vanishingly small (p<0.0001 Fishers exact test)

iv) Blue cone monochromasy

In 1989, Nathans, et al. (*Science* 245: 831–838) reported a genetic analysis of men with blue cone monochromasy, a disease in which none of the red and green pigment genes on the X-chromosome are expressed. For all patients except one reported in that study, the underlying cause of the vision defect was identified. In the one case, it was noted that the person had a single visual red cone pigment gene and no green genes and that the encoded pigment had two amino acid substitutions specified by exon 3. Nathans, et al. postulated that because the amino acid substitutions identified were conserved changes, they were unlikely to underlie the disease in that patient. However, the amino acid combination specified by the pigment gene in that patient is one that we would call a poison sequence, and thus despite the conserved nature of the specific changes, the combination causes the defect. The amino acid combination for this patient is shown in Table 2 in the column labeled B-cone monochromat.

We have now looked at the genes in several other blue cone monochromats and we have found that the defect can be accounted for by "poison combinations" in all patients who do not have one of the types of defects that were identified by Nathans and colleagues (defects described by Nathans and colleagues are in *Science* 245: 831–838 and *American Journal of Human Genetics* 53: 987–1000).

Figure 6:
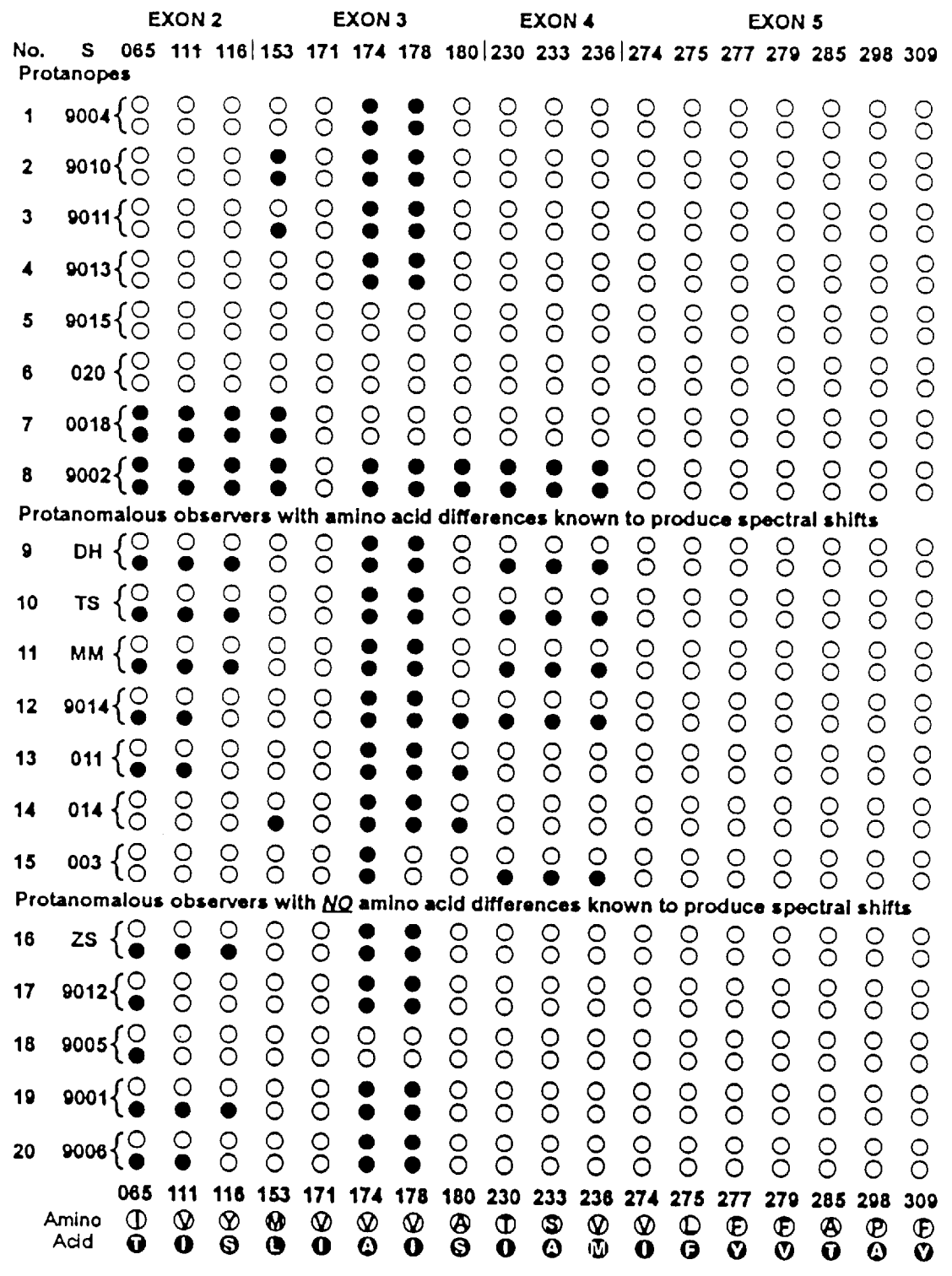

C. Correlation of Amino Acid Position at the 18 Dimorphic Positions and Protan Vision Disorders FIG. 6 is a tabulation of amino acid sequence at the 18 dimorphic positions and various protan vision disorders obtained for 20 men with protan vision disorders. As FIG. 6 demonstrates, one may correlate the amino acid specified at the 18 dimorphic sites with the occurrence and severity of the protan disorder. The patients with differences in their genes in exons 2, 3, and 4 are less severely affected than patients who do not have these differences.

D. Paper and Pencil Vision Test

The following is a description of a paper and pencil vision test and we have found to be especially useful when combined with the molecular biological tests described above.

This test is to be taken under fluorescent light or daylight (or a combination of the two. Do not take this test under incandescent light.

STEP 1. Look at the test page (FIG. 4). Each square contains 4 large dots and a number of smaller gray dots. Some of the large dots are colored, others are gray. Below each square is a line. This line is used to rate the color of the most colored large dot in each square. Look over the whole sheet and pick out three squares containing the colored dots that stand out as being the most colored to you. Identify them by placing a mark at the right most end of the line (as shown below). This indicates that these colored dots are among the most highly colored on the page. (There may be more than three dots that you see as the most highly colored, you will mark them the same way in step 3).

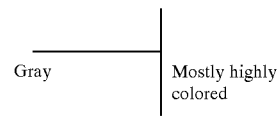

STEP 2. In some of the squares there are no colored dots, that is, all the dots are gray. Identify one of these by making a mark on the left most side of the line below these squares (as shown below). (There may be more than one square with no colored dots, you will mark them the same way in step 3).

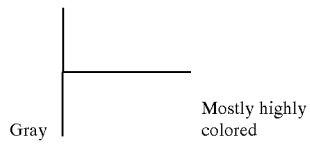

STEP 3. For each of the remaining squares, pick out the most colored dot in the square and rate the color of the dot you picked on the line below the square. Scale your rating according to the extremes you have already chosen in steps 1 and 2. If the dot is about half as colored as the most colored dots on the page, make a mark about half-way between the two ends. If the dot has very little color compared to the most colored dots, make a mark very near the gray end of the line. (Some examples are shown below.)

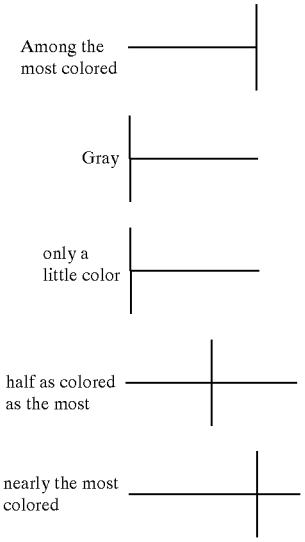

We claim:

1. A method of detecting cone-photoreceptor-based vision disorders, comprising the steps of
   a) examining the amino acid sequence of a patient's red or green photopigments, and
   b) correlating the amino acid sequence with amino acid combinations associated with vision disorder,
   wherein the amino acid sequence is the sequence at positions selected from the group consisting of codon positions 65, 111, 116, 153, 171, 174, 178, 180, 230, 233, 236, 274, 275, 277, 279, 285, 298, and 309 of the gene encoding the red or green photopigment and wherein the correlation comprises comparison of the amino acid sequence with amino acid sequences shown to be diagnostic of vision disorders.

2. The method of claim 1 wherein the examination of the amino acid sequence is by examination of photopigment genes.

3. The method of claim 1 wherein the sequence at positions 153, 171, 174, and 180 can be correlated with a diagnosis of age-related macular degeneration.

4. The method of claim 1 wherein the sequence at positions 153, 171, 174, 178, and 180 can be correlated with a diagnosis of deuteranomaly cone, degeneration, or B-cone monochromat condition.

5. A method of detecting red-green vision disorders and determining the severity of the disorder, comprising the steps of
   a) examining the predicted spectral separation of L and M pigments encoded by a patient's photoreceptor genes, and
   b) correlating the spectral separation with a degree of vision disorder, wherein a spectral separation of greater than 8 nM is predictive of very mild red-green color blindness disorder, a separation of 5 nM–8 nM is predictive of mild vision disorder, a separation of 1 nM–4 nM is predictive a severe disorder and a separation of less than 1 nM is predictive of very severe disorder.

6. The method of claim 5 wherein the examination comprises analyzing the patient's photopigment genes at codon positions 65, 111, 116, 153, 171, 174, 178, 180, 230, 233, 236, 274, 275, 277, 279, 285, 298 and 309 of the genes encoding the red or green photopigment.

* * * * *

UNITED STATES PATENT AND TRADEMARK OFFICE
CERTIFICATE OF CORRECTION

PATENT NO. : 5,837,461  Page 1 of 1
DATED : November 17, 1998
INVENTOR(S) : Neitz et al.

It is certified that error appears in the above-identified patent and that said Letters Patent is hereby corrected as shown below:

Column 1,
Line 8, insert the following:
-- STATEMENT REGARDING FEDERALLY SPONSORED RESEARCH OR DEVELOPMENT
The U.S. government has a paid-up license in this invention and the right in limited circumstances to require the patent owner to license others on reasonable terms as provided for by the terms of contract Nos. EY09303 and EY09620, both awarded by the National Eye Institute of the National Institutes of Health. --

Signed and Sealed this

Thirtieth Day of September, 2003

JAMES E. ROGAN
*Director of the United States Patent and Trademark Office*

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Oligonucleotide ( x i ) SEQUENCE DESCRIPTION: SEQ ID NO:1:

GAGGCGAGGC TACGGAGT    18

( 2 ) INFORMATION FOR SEQ ID NO:2:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Oligonucleotide ( x i ) SEQUENCE DESCRIPTION: SEQ ID NO:2:

ACGGTATTTT GATGTGGATC TGCT    24

( 2 ) INFORMATION FOR SEQ ID NO:3:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( x i ) SEQUENCE DESCRIPTION: SEQ ID NO:3:

TTAGTCAGGC TGGTCGGGAA CT    22

( 2 ) INFORMATION FOR SEQ ID NO:4:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( i i ) MOLECULE TYPE: Oligonucleotide ( x i ) SEQUENCE DESCRIPTION: SEQ ID NO:4:

CATGATGATA GCGAGTGGGA TG    22

( 2 ) INFORMATION FOR SEQ ID NO:5:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( i i ) MOLECULE TYPE: Oligonucleotide ( x i ) SEQUENCE DESCRIPTION: SEQ ID NO:5:

CCTTCGAAGG CCCGAATTA 19

( 2 ) INFORMATION FOR SEQ ID NO:6:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:6:

```
Ile Phe Thr Val Thr Ala Tyr
1               5
```

( 2 ) INFORMATION FOR SEQ ID NO:7:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:7:

```
Val Leu Phe Phe Ala Pro Phe
1               5
```

( 2 ) INFORMATION FOR SEQ ID NO:8:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:8:

```
Leu Val Ala Val Ala
1               5
```

( 2 ) INFORMATION FOR SEQ ID NO:9:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Leu Val Ala Ser
1
```

( 2 ) INFORMATION FOR SEQ ID NO:10:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Leu Val Ala Val Ala
```

( 2 ) INFORMATION FOR SEQ ID NO:11:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

Met  Val  Ala  Ile  Ala  Thr  Ser  Val
    1                        5

( 2 ) INFORMATION FOR SEQ ID NO:12:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

Met  Val  Val  Val  Ala  Thr  Ser  Val
    1                        5

( 2 ) INFORMATION FOR SEQ ID NO:13:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

Leu  Val  Ala  Ile  Ala  Thr  Ser  Val
    1                        5

( 2 ) INFORMATION FOR SEQ ID NO:14:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:14:

Leu  Val  Ala  Ile  Ser  Thr  Ser  Val
    1                        5

( 2 ) INFORMATION FOR SEQ ID NO:15:

( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

Met  Val  Ala  Ile  Ala  Ile  Ala  Met (2) INFORMATION FOR SEQ ID NO:16:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:16:

Leu Ile Ala Ile Ser Thr Ser Val
    1               5

(2) INFORMATION FOR SEQ ID NO:17:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:17:

Met Val Ala Ile Ser Thr Ser Val
    1               5

(2) INFORMATION FOR SEQ ID NO:18:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:18:

Met Val Val Ile Ala Thr Ser Val
    1               5